United States Patent [19]

Koyama et al.

[11] Patent Number: 4,576,793

[45] Date of Patent: Mar. 18, 1986

[54] ANALYTICAL ELEMENT

[75] Inventors: Mikio Koyama; Kenichiro Okaniwa; Masakuni Saruhashi, all of Hino, Japan

[73] Assignee: Konishiroku Photo Industry Co., Ltd., Tokyo, Japan

[21] Appl. No.: 527,681

[22] Filed: Aug. 29, 1983

[30] Foreign Application Priority Data

Sep. 7, 1982 [JP] Japan .................................. 57-156084

[51] Int. Cl.$^4$ ............................................. G01N 21/78
[52] U.S. Cl. ......................................... 422/56; 422/55; 435/805; 436/169; 436/170
[58] Field of Search ...................... 422/56, 57, 58, 60, 422/69, 86, 55; 436/169, 170; 435/805

[56] References Cited

U.S. PATENT DOCUMENTS 4,258,001  3/1981  Pierce et al. ...................... 435/805

FOREIGN PATENT DOCUMENTS 3133538  5/1982  Fed. Rep. of Germany ........ 422/60

Primary Examiner—Barry S. Richman
Assistant Examiner—C. M. Delahunty
Attorney, Agent, or Firm—Frishauf, Holtz, Goodman & Woodward

[57] ABSTRACT

There is disclosed an analytical element comprising a support; a reagent layer which is positioned on one side of the support and contains a reagent reactive with a component in a fluid sample; and a porous spreading layer which is positioned on the reagent layer on the opposite side to that of the support for permitting the component in the fluid sample to permeate into the reagent layer; wherein at least one layer contains 5% by weight or more of a polymer formed by, (i) a copolymerizable ethylenically unsaturated acid with (ii) a copolymerizable ethylenically unsaturated monomer.

The analytical element according to the present invention can determine a component in a fluid sample quantitatively.

17 Claims, No Drawings

ANALYTICAL ELEMENT

This invention relates to analytical chemistry, particularly to an analytical element for analysis of a predetermined specific component in a fluid.

There have been developed a large number of methods for analysis of test components in testing of a fluid sample. These methods may be classified broadly into a solution system in which the reaction is carried out in a solution and a solid phase system in which the reaction is carried out in a carrier of a solid phase.

The analytical reaction in a solution reaction system includes a large number of procedures, varying widely from an analytical procedure of the so-called manual method in which no machine is used at all to an automatic quantitative analyzer procedure in which the operations used are fully automatic except for the initial injection of a sample. For example, the automatic quantitative analyzer as disclosed in U.S. Pat. No. 2,797,149 is typical of these automatic analyzers and has been used widely in the field of clinical tests.

These analyzers, while they are useful instruments, involve the drawbacks that skilled artisans are required for this operation, and also that an enormous amount of labor is necessary for maintenance of the instruments.

On the other hand, the analytical reactions in solid phase have also been widely employed. For example, typical of these methods which are well known in the art are pH test papers or analytical test papers as disclosed in U.S. Pat. No. 3,050,373.

The above test paper is prepared by impregnating a water-absorptive carrier such as filter paper with a reagent solution, followed by drying. By the use of the above test paper, a fluid sample is added dropwise on said test paper, or said test paper is dipped in a fluid sample, and the color change or density change of the test strip is measured by judgement with the naked eye or by means of a reflection densitometer to determine the concentration level of a specific component in the fluid sample.

These test papers are useful, since they are easy in handling and can give the result of test directly, but its usefulness is limited in the field of semi-quantitative analysis or qualitative analysis due to its constitution.

As contrasted to the analytical method of the prior art as described above, there is also proposed an analytical element for blood as disclosed in Japanese Patent Publication No. 21677/1978, in which an analytical reaction in solid phase which is easy in handling is utilized and also has a high quantitative performance.

This is an analytical element for blood, which comprises at least one reagent layer which is positioned on one side of a light-transmissive and liquid-impervious support, contains at least one reagent reactive with a component in a fluid sample and is constituted of a hydrophilic colloid and at least one porous medium layer of a non-fibrous material which is positioned on the reagent layer on the opposite side to that of said support for permitting the component in said fluid sample to permeate into said reagent layer.

In the above analytical element, a reagent is provided in the reagent layer, and when ready for practical use, a certain quantity of a fluid sample can be added dropwise to the above spreading layer, and after a certain period of time, the concentration of a specific component in the fluid sample can be determined from the color forming density in the reagent layer. This evidently indicates that the pH in the reagent layer participating in the analytical reaction is required to be maintained at a constant value. For this reason, said Patent Publication describes incorporation of a buffering agent. However, if a fluid sample is supplied through said porous medium layer, undesirable capillary phenomenon gives rise to diffusion of the buffering agent, thus failing to give the expected buffering effect.

Further, as another disadvantage, when various analytical reactions occur on the above analytical element, the analytical reactions in the acidic region by incorporation of a mineral acid in a reagent layer are not desirable, because the reagent layer comprising a hydrophilic colloid substance is deteriorated in film strength by an acid.

In order to overcome the drawbacks as mentioned above, the present inventors have made extensive studies, and consequently overcome said drawbacks by the use of an analytical element having the constitution as shown below.

That is, the present invention provides an analytical element, comprising a support; a reagent layer which is positioned on one side of said support and contains a reagent reactive with a component in a fluid sample; and a porous spreading layer which is positioned on the reagent layer on the opposite side to that of said support for permitting the component in said fluid sample to permeate into said reagent layer; wherein at least one layer contains 5% by weight or more of a polymer formed by (i) a a copolymerizable ethylenically unsaturated acid with (ii) a copolymerizable ethylenically unsaturated monomer.

This invention is described in further detail below.

Preferable monomers of copolymerizable ethylenically unsaturated acids (i) to be used in this invention are those having at least one carboxyl group, sulfo group or phosphono group. Among those having carboxyl groups or sulfo groups, those preferable have one or two carboxyl group(s) or sulfo group(s), particularly the monomers represented by the following formula [I]:

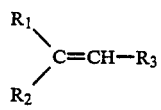

Formula [I]

wherein $R_1$ represents a carboxyl group, a sulfo group or a group having a carboxyl group or a sulfo group, $R_2$ represents a hydrogen atom or an alkyl group and $R_3$ represents a hydrogen atom or an alkoxycarbonyl group.

When $R_1$ is carboxyl group or sulfo group it is preferably sulfophenyl group, sulfoalkyloxycarbonyl group (the alkyl moiety having preferably 1 to 4 carbon atoms) or sulfoalkylcarbamoyl group (the alkyl moiety having preferably 1 to 5 carbon atoms).

The alkyl group in $R_2$ may have substituents, preferably including alkoxycarbonyl groups and carboxyl groups. Illustrative of preferable alkyl groups are methyl group, alkoxycarbonylmethyl groups containing an alkoxy group having 1 to 4 carbon atoms and carboxymethyl group.

As the alkoxycarbonyl groups represented by $R_3$ those having 2 to 5 carbon atoms are preferred.

As the monomers represented by the formula [I], there may be included, for example, acrylic acid, methacrylic acid, itaconic acid, itaconic acid mono-alkyl esters (preferably esters of alkyls having 1 to 4 carbon atoms such as monomethyl itaconate, monobutyl itaconate), maleic acid mono-alkyl esters (preferably esters of alkyls having 1 to 4 carbon atoms such as monomethyl maleate, monobutyl maleate), styrene sulfonic acid, acryloyloxyalkyl sulfonic acids (e.g. acryloyloxypropyl sulfonic acid, acryloyloxyethyl sulfonic acid), methacryloyloxyalkyl sulfonic acids (e.g. methacryloyloxypropyl sulfonic acid, methacryloyloxybutyl sulfonic acid), acrylamide alkyl sulfonic acid (e.g. 2-acrylamide-2-methylethane sulfonic acid, 2-acrylamide-2-methylbutane sulfonic acid), methacrylamide alkyl sulfonic acid (e.g. 2-methacrylamide-2-methylethane sulfonic acid) and so on.

Among the preferable monomers represented by the formula [I], are those having 1 or 2 carboxyl group, for example, acrylic acid, methacrylic acid, itaconic acid, monomethyl maleate, particularly acrylic acid, methacrylic acid and itaconic acid. Above all, acrylic acid and itaconic acid are most preferred.

The preferable monomers having phosphono group among the copolymerizable ethylenically unsaturated acid monomers (i) of this invention are those having one phosphono group, especially those represented by the following formula [II]:

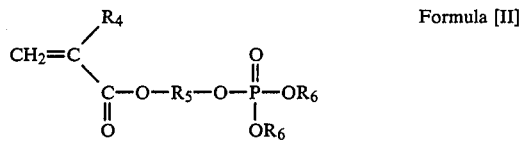

Formula [II]

wherein $R_4$ represents a hydrogen atom or a methyl group, $R_5$ represents an aliphatic hydrocarbon group having 2 to 10 carbon atoms or $-(R_7-O)_{\overline{m}}R_7-$ (where $R_7$ is an aliphatic hydrocarbon group having 2 to 6 carbon atoms and m is an integer of 1 to 5)
and $R_6$ represents a hydrogen atom.

As the aliphatic hydrocarbon group represented by $R_5$ or $R_7$, an alkylene group is preferred, which alkylene group may also be branched or have a halogen atom such as chlorine atom, a lower alkoxy group such as ethoxy group or an aryl group such as phenyl group as the substituent.

Preferable examples of the monomers represented by the formula [II] include 2-acryloyloxyethyl phosphate, 1-methyl-2-acryloyloxyethyl phosphate, 2-acryloyloxyethoxyethyl phosphate, 4-acryloyloxybutyl phosphate, 2-methacryloyloxyethyl phosphate, 1-methyl-2-methcryloyloxyethyl phosphate, 1-chloromethyl-2-methcryloyloxyethyl phosphate, 2-methacryloyloxyethoxyethyl phosphate, 4-methacryloyloxybutyl phosphate and the like. Particularly, 2-methacryloyloxyethyl phosphate and 2-acryloyloxyethyl phosphate are preferred.

The monomeric units of the copolymerizable ethylenically unsaturated acids (i) represented by the above formulae [I] and [II] should preferably be contained in an amount of 5% by weight or more of the polymer containing said unsaturated acid.

More preferably, they should be contained in an amount of 25% by weight or more, most preferably 45% by weight or more. With a content less than 5% by weight, no sufficient effect as the analytical element of this invention can be exhibited. Further, it is also possible to copolymerize two or more kinds of the above ethylenically unsaturated acids of this invention.

The polymer of this invention can contain various monomeric units in addition to the above ethylenically unsaturated acids copolymerized therein depending on its purpose.

Preferable as the additional copolymerizable ethylenically unsaturated monomers (ii) constituting the polymer of this invention are ethylenically unsaturated nitriles, styrenes, ethylenically unsaturated acid esters, ethylenically unsaturated acid amides, conjugated dienes, vinyl heterocyclic compounds, halo-substituted ethylenes and cross-linkable monomers.

As the ethylenically unsaturated nitriles, there may be included preferably those represented by the following formula [III]:

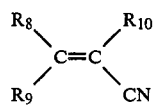

Formula [III]

wherein $R_8$ and $R_9$ each represent a hydrogen atom or a halogen atom, $R_{10}$ represents a halogen atom, an alkyl group, an alkoxy group, an acyloxy group, an aryl group, a cyano group or a carbamoyl group.

Preferable as $R_8$ and $R_9$ are hydrogen atoms and fluorine atoms, particularly hydrogen atoms. Illustrative of the halogen atom represented by $R_{10}$ are fluorine atom, chlorine atom and bromine atom. The alkyl group represented by $R_{10}$ preferably is a lower alkyl group having 1 to 5 carbon atoms, such as methyl, trifluoromethyl, ethyl, iso-propyl, n-propyl, n-amyl and the like. The alkoxy group represented by $R_{10}$ preferably has 1 to 3 carbon atoms, as exemplified by methoxy group. The acyloxy group represented by $R_{10}$ preferably is an alkylcarbonyloxy group having 2 to 4 carbon atoms, as exemplified by acetoxy group. The aryl group represented by $R_{10}$ preferably is a phenyl group (this phenyl group may also have as the substituent a cyano group, a halogen atom such as chlorine atom, a lower alkyl group such as methyl group or a lower alkoxy group such as methoxy group), as exemplified by phenyl, methoxyphenyl, methylphenyl, chlorophenyl, cyanophenyl and the like. Of the groups represented by $R_{10}$, the preferable ones are hydrogen atom, halogen atoms and alkyl groups, particularly hydrogen atom.

Typical examples of the monomers represented by the formula [III] may include acrylonitrile, methacrylonitrile, α-chloroacrylonitrile, α-bromoacrylonitrile, α-fluoroacrylonitrile, α-chloro-β-difluoroacrylonitrile, α-trifluoromethyl acrylonitrile, α-ethylacrylonitrile, α-isopropyl acrylonitrile, α-n-propyl acrylonitrile, α-n-amyl acrylonitrile, α-methoxy acrylonirile, α-acetoxy acrylonitrile, α-phenyl acrylonitrile, α-cyanophenyl acrylonitrile, α-chlorophenyl acrylonitrile, α-methylphenyl acrylonitrile, α-methoxyphenyl acrylonitrile and vinylidene cyanide.

Preferable styrenes may be represented by the following formula [IV]:

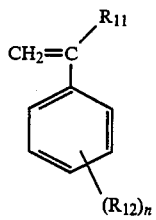

Formula [IV]

wherein $R_{11}$ represents a hydrogen atom, a halogen atom or an alkyl group, $R_{12}$ represents a hydrogen atom, a halogen atom, an alkyl group, an alkoxy group, a cycloalkyl group, an alkoxycarbonyl group or an acyloxylalkyl group, and n is an integer of 1 to 5.

As the alkyl group represented by $R_{11}$, an alkyl group having 1 or 2 carbon atoms is preferred.

The alkyl group represented by $R_{12}$ preferably has 1 to 6 carbon atoms, alkoxy group of 1 to 4, carbon atoms, cycloalkyl group of 5 to 6, carbon atoms alkoxycarbonyl group with an alkyl moiety having 1 to 2 carbon atoms, the acyloxy-alkyl group with an acyl moiety having 2 to 3 carbon atoms and the acyloxyalkyl group with an alkyl moiety having 1 to 2 carbon atoms. Preferably, n is 1 or 2.

More specifically, the styrenes represented by the formula [IV] are inclusive of styrene, p-methylstyrene, α-methyl styrene, p-chlorostyrene, p-chloromethylstyrene, m-chloromethylstyrene, m-methylstyrene, m-ethylstyrene, p-ethylstyrene, 2,5-dimethylstyrene, 3,4-dimethylstyrene, 3,5-dimethylstyrene, m-iso-propylstyrene, p-iso-propylstyrene, p-butylstyrene, m-t-butylstyrene, p-hexylstyrene, p-cyclohexylstyrene, m-methoxystyrene, 4-methoxy-3-methylstyrene, p-ethoxystyrene, 3,4-dimethoxystyrene, m-chlorostyrene, 3,4-dichlorostyrene, 3,5-dichlorostyrene, m-bormostyrene, p-bromostyrene, 3,5-dibromostyrene, 4-fluoro-3-trifluoromethyl styrene, 2-bromo-4-trifluoromethyl styrene, p-methoxycarbonyl styrene, p-acetoxymethyl styrene and the like.

As the ethylenically unsaturated acid esters, ethylenically unsaturated carboxylic acid esters are preferred, particularly those represented by the following formula [V]:

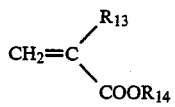

Formula [V]

wherein $R_{13}$ represents a hydrogen atom or a methyl group, and $R_{14}$ represents an alkyl group or a phenyl group.

As said alkyl group, an alkyl group having 1 to 8 carbon atoms, particularly 1 to 4 carbon atoms, is preferred.

Typical examples of the monomers represented by the formula [V] include methyl acrylate, ethyl acrylate, n-butyl acrylate, n-propyl acrylate, iso-butyl acrylate, sec-butyl acrylate, 2-hydroxyethyl acrylate, 2-hydroxypropyl acrylate, 2-ethylhexyl acrylate, hexyl acrylate, 2-phenoxyethyl acrylate, 2-chloroethyl acrylate, dimethylaminoethyl acrylate, benzyl acrylate, cyclohexyl acrylate, phenyl acrylate, 2-hydroxypropyl acrylate, tetrahydrofuryl acrylate, 2,3-dihydroxypropyl acrylate, methyl methacrylate, ethyl methacrylate, n-butyl methacrylate, propyl methacrylate, 2-hydroxyethyl methacrylate, 2-hydroxypropyl methacrylate, isobutyl methacrylate, acetoxyethyl methacrylate, dimethylaminoethyl methacrylate, chlorobenzyl methacrylate, octyl methacrylate, furfuryl methacrylate, phenyl methacrylate, and the like.

As the ethylenically unsaturated acid amides, there are included acrylamides and methacrylamides. Examples of acrylamides are acrylamide, diacetone acrylamide, methylol acrylamide and methyl acrylamide.

Examples of methacrylamides are methacrylamide and benzyl methacrylamide.

The copolymerizable conjugated diene monomers to be used preferably in this invention are monomers represented by the following formula [VI]:

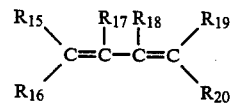

Formula [VI]

wherein $R_{15}$ through $R_{20}$ individually represent a hydrogen atom, a halogen atom, an alkyl group, an aryl group, a cyano group or a group

—$COOR_{21}$ (where $R_{21}$ represents an alkyl group).

The preferable halogen atoms represented by $R_{15}$ through $R_{20}$ are chlorine atom and bromine atom.

The alkyl group represented by $R_{15}$ through $R_{21}$ preferably is a lower alkyl, particularly a lower alkyl having 1 to 4 carbon atoms. Among these, methyl is the most preferred. The alkyl group represented by $R_{15}$ through $R_{21}$ may also have a substituent, but preferably it is unsubstituted.

The aryl group represented by $R_{15}$ through $R_{20}$ preferably is a phenyl group, which may also have a substituent. Preferable substituents include halogen atoms (preferably chlorine atom, bromine atom) and alkyl groups (preferably those having 1 to 3 carbon atoms, particularly methyl group).

Among the various atoms and groups as $R_{15}$ through $R_{20}$ enumerated above, the preferable ones are hydrogen atom, halogen atoms or alkyl groups.

The total carbon number in the monomer represented by the above formula [VI] preferably is 4 to 12, more preferably 4 to 9, particularly preferably 4 to 6. It is also preferred that at least two of the groups $R_{15}$ through $R_{20}$ be hydrogen atoms.

Illustrative of the monomers represented by the formula [VI] are 1,3-butadiene, alkyl- (preferably lower alkyl having 1 to 4 carbon atoms) substituted 1,3-butadiene (e.g. isoprene, 1,3-pentadiene, 2-ethyl-1,3-butadiene, 2-n-propyl-1,3-butadiene, 2-n-butyl-1,3-butadiene, 2,3-dimethyl-1,3-butadiene, 2-methyl-1,3-pentadiene, 4-methyl-1,3,-pentadiene, etc.), aryl- (preferably phenyl-) substituted 1,3-butadiene (e.g. 1-phenyl-1,3-butadiene, 2-phenyl-1,3-butadiene, 1-(p-chlorophenyl)-1,3-butadiene, 1-phenyl-2-carbomethoxy-1,3-butadiene, 2-p-tolyl-1,3-butadiene, etc.), halo- (preferably chloro-, bromo-) substituted 1,3-butadiene (e.g. 1-chloro-1,3-butadiene, 2-chloro-1,3-butadiene, 1-bromo-1,3-butadiene, 2-bromo-1,3-butadiene, 1,1-dichloro-1,3-butadiene, 2,3-dichloro-1,3-butadiene, 2,3-dibromo-1,3-butadiene, 1,1,2-trichloro-1,3-butadiene, 1,1,2,3-tetrachloro-1,3-butadiene, etc.), cyano-substituted 1,3-butadiene (e.g. 1-cyano-1,3-butadiene, 2-cyano-1,3-butadiene, etc.).

Among these various kinds of conjugated dienes, particularly preferred are 1,3-butadiene, alkyl- (particularly, methyl-) or halo-substituted 1,3-butadiene, particularly 1,3-butadiene, isoprene, 2,3-dimethyl-1,3-butadiene, most preferably isoprene or 2,3-dimethyl-1,3-butadiene.

Vinyl heterocyclic compounds include, for example, N-vinyl pyrrolidone, N-vinylimidazole, vinyl pyridines (e.g. 4-vinyl pyridine, 2-vinyl pyridine, etc.).

As the halo-substituted ethylenes, for example, vinyl chloride, vinylidene chloride, vinyl fluoride, vinylidene fluoride, tetrafluoroethylene and the like can be employed.

Examples of the cross-linkable monomers are divinylbenzene, ethyleneglylol dimethacrylate, trimethylolpropane triacrylate and pentaerythritol trimethacrylate.

The polymer of this invention may be prepared by homopolymerization of the copolymerizable ethylenically unsaturated acid monomer (i) of this invention or by copolymerization of said acid monomer with another ethylenically unsaturated monomer.

Exemplary polymers of this invention are enumerated below, but the present invention is not limited by these polymers.

Exemplarly polymers (1) Polyacrylic acid
(2) Copoly(acrylic acid—n-butyl acrylate) (Weight ratio 3:1)
(3) Copoly(acrylic acid—ethyl acrylate) (Weight ratio 2:1)
(4) Copoly(acrylic acid—methyl acrylate) (Weight ratio 3:1)
(5) Copoly(acrylic acid—vinylidene chloride) (Weight ratio 3:1)
(6) Copoly(acrylic acid—styrene—methyl acrylate) (Weight ratio 5:2:3)
(7) Polymethacrylic acid
(8) Copoly(methacrylic acid—n-butyl acrylate) (Weight ratio 3:1)
(9) Copoly(methacrylic acid—n-butyl methacrylate) (Weight ratio 9:1)
(10) Copoly(methacrylic acid—acrylonitrile—styrene) (Weight ratio 5:1:4)
(11) Copoly(methacrylic acid—styrene—divinylbenzene) (Weight ratio 95:4:1)
(12) Copoly(methacrylic acid—ethyl acrylate) (Weight ratio 4:1)
(13) Copoly(itaconic acid—ethyl acrylate) (Weight ratio 1:1)
(14) Copoly(itaconic acid—styrene) (Weight ratio 1:1)
(15) Copoly(mono-butyl itaconate—methyl acrylate) (Weight ratio 1:1)
(16) Copoly(mono-butyl maleate—ethylene) (Weight ratio 76:24)
(17) Copoly(mono-butyl maleate—styrene) (Weight ratio 62:38)
(18) Copoly(acrylic acid—acrylonitrile—vinylidene chloride) (Weight ratio 15:15:70)
(19) Polystyrene sulfonic acid
(20) Copoly(styrene sulfonic acid—divinyl benzene) (Weight ratio 98:2)
(21) Copoly(styrene sulfonic acid—methyl acrylate) (Weight ratio 1:1)
(22) Copoly(styrene sulfonic acid—styrene) (Weight ratio 2:1)
(23) Polyacryloyloxypropyl sulfonic acid
(24) Polyacryloyloxyethyl sulfonic acid
(25) Poly-2-acrylamide-2-methylethane sulfonic acid
(26) Poly-2-methacrylamide-2-methylethane sulfonic acid
(27) Copoly(acryloyloxypropyl sulfonic acid—n-butyl acrylate) (Weight ratio 4:1)
(28) Copoly(2-acrylamide-2-methylethane sulfonic acid—n-butyl acrylate) (Weight ratio 4:1)
(29) Copoly(2-acrylamide-2-methylethane sulfonic acid—n-butyl acrylate) (Weight ratio 1:1)
(30) Copoly(2-acrylamide-2-methylethane sulfonic acid—styrene) (Weight ratio 1:1)
(31) Copoly(2-acrylamide-2-methylethane sulfonic acid—acrylamide) (Weight ratio 1:1)
(32) Poly-2-acryloyloxyethyl phosphate
(33) Poly-2-methacryloyloxyethyl phosphate
(34) Copoly(2-acryloyloxyethyl phosphate—styrene) (Weight ratio 1:1)
(35) Copoly(2-acryloyloxyethyl phosphate—n-butyl acrylate) (Weight ratio 4:1)
(36) Copoly(2-methacryloyloxyethyl phosphate—acrylonitrile—methyl acrylate) (Weight ratio 5:1:4)

The exemplary polymers set forth above can be easily prepared by polymerization with a radical polymerization initiator. For example, various techniques such as solution polymerization, suspension polymerization, emulsion polymerization and other techniques are be used depending on the purposes. Further, it is also possible to form the acid moiety in the polymer of this invention by introducing it into a trunk polymer by way of a polymerization reaction or by way of a previous conversion of a certain group.

The following synthesis examples illustrate preparation of the exemplary compounds of this invention.

SYNTHESIS EXAMPLE 1

Preparation of exemplary compound (3)

500 ml of toluene was charge into a four-necked flask equipped with a stirrer, a cooling tube, a thermometer and a nitrogen inlet tube, and heated to 65° C. with stirring under flow of nitrogen after which a solution of 60 g of acrylic acid, 30 g of ethyl acrylate and 2 g of benzoyl peroxide dissolved in 100 ml of toluene over about 30 minutes was added dropwise gradually from a dropping funnel. The mixture was stirred as such at 65° C. for 24 hours to carry out the reaction.

After completion of the reaction, the inner temperature was lowered to room temperature, followed by filtration by No. 2 glass filter. The product remaining on the filter was washed several times with toluene on the filter and then dried under vacuum to obtain the desired product. Yield: 89.3%

SYNTHESIS EXAMPLE 2

Preparation of examplary compound (28)

A solution of 48 g of 2-acrylamide-2-methylethane sulfonic acid, 12 g of n-butyl acrylate and 0.06 g of azobisisobutyronitrile dissolved in 400 ml of methanol was charged into a pressure bottle of 500 ml capacity. After replacement of the pressure bottle with nitrogen, the bottle was sealed and left to stand in an oven at 60° C. for 24 hours. After completion of the reaction, the inner temperature was lowered to room temperature, and methanol was removed by an evaporator. The white solids formed were dissolved in 100 ml of pure water, packed in a cellulose semi-permeable tube and dialyzed in pure water bath for 72 hours to remove unaltered monomers, followed by removal of H$_2$O by an evaporator and vacuum drying, to give a desired product of a white polymer.

Yield: 75.6%

The polymer of this invention can be added as a part in the reagent layer, as a matter of course, and further it can be used alone as a layer, since the polymer per se has sufficient film forming property.

It is also possible to use the polymer of this invention as not only an ordinary linear polymer alone but also a mixture of other binders with the linear polymer or an insoluble polymer such as in the form of a polymeric latex. Furthermore, non-dispersible particulate polymers such as ion-exchange resins may be introduced into the layer as such or after micropulverization, if desired. Preferably, however, the polymer is desirably used in the form of a linear polymer or a polymer latex.

When the polymer of this invention is to be used as a mixture with other binders, it is mixed in an amount of at least 5% by weight, preferably 10% by weight or more based on other binders.

Various binders may be available, including, for example, gelatin or gelatin derivatives such as phthalated gelatin; polyvinyl alcohol; vinyl alcohol copolymers such as partial hydrolyzates of polyvinyl acetates; ethylenically unsaturated amides such as polyacrylamide, polymethacrylamide, etc.; vinyl heterocyclic compounds such as polyvinyl pyrrolidone, polyvinyl imidazole, and the like.

The polymer of this invention itself acts as an acid and permits an analytical reaction to occur at a low pH, and at the same time forms a buffering agent in co-operation with other low molecular weight compounds, thereby acting as an immobilized buffering agent.

The layer containing the polymer of this invention can also incorporate other reagents depending on the purpose. When other reagents are to be incorporated, they can be easily contained in the layer by dissolving or dispersing such reagents in the solution containing the polymer of this invention. The dispersing method employed here may be chosen from a variety of methods known in the art depending on the properties of the reagent to be incorporated such as direct dispersion method, oil protect dispersion method, etc.

The reagent layer containing no polymer of this invention comprises preferably a hydrophilic colloidal substance. As hydrophilic colloidal substances, there may be employed, for example, gelatin, gelatin derivatives such as phthalated gelatin, polyvinyl alcohol, polyvinyl pyrrolidone, polyacrylamide, and so on.

Further, into the above layer, a polymer latex as disclosed in Japanese Provisional Patent Publications No. 50393/1979 or No. 99752/1983 may also be added, if desired. By addition of such a latex, not only can the stability of the reagents be improved, but also film properties of the layer comprising a hydrophilic colloidal substance can be improved.

Further, it is possible to add various additives into the reagent layer in the analytical element of this invention. For example, there may be added surfactants, preservatives, buffering agents, film hardeners, etc., if desired.

Particularly, surfactants can be used effectively for various purposes such as controlling of the permeation speed by aiding in uniform distribution of a fluid sample throughout the reagent layer.

As useful surfactants, there may be employed all surfactants, either ionic(anionic or cationic) or nonionic, but preferably nonionic surfactants are more effective. Examples of nonionic surfactants are polyalkyleneglycol derivatives of alkyl-substituted phenols such as 2,5-di-t-butylphenoxy polyethyleneglycol, p-octylphenoxy polyglycidylether and p-iso-nonylphenoxy polyethylene glycol, and polyalkyleneglycol esters of higher fatty acids. These surfactants have the effect of controlling the permeation speed of a liquid sample into the reagent layer simultaneously with the effect of inhibiting generation of undesirable "chromatography phenomenon". A further effect of a surfactant is alleviating various undesirable influences by proteins contained in a biological fluid sample.

The above surfactant may be employed in an amount which can be widely varied, but generally in an amount of 0.005% to 10% by weight based on the weight of the polymer, preferably 0.05% to 6% by weight.

The reagent layer of the present invention, including other layers, may be applied by various coating methods such as the dip coating method, the air knife method, the curtain coating method or the extrusion coating method using a hopper as disclosed in U.S. Pat. No. 2,681,294. If desired, two or more layers may be coated simultaneously according to the method as disclosed in U.S. Pat. No. 2,761,791 and U.K. Pat. No. 837,095.

The drying temperature may be chosen as desired depending on the properties of the reagent contained. For example, when a physiologically active substance such as an enzyme is contained, a temperature of about 50° C. or lower, preferably about 45° C. or lower may be employed. Otherwise, any temperature up to the limit of about 100° C. may be employed.

When the analytical element of this invention has another reagent layer in addition to the reagent layer containing the polymer of this invention, they can be layered in the order which may be selected depending on the analytical reaction employed. That is, it is possible to take various modes such as support/the reagent layer containing the polymer of this invention/another reagent layer and support/another reagent layer/the reagent layer containing the polymer of this invention.

The support according to the analytical element of the present invention (hereinafter abbreviated as the support according to the present invention) is any kind of support, so long as it is impervious to liquids and light-transmissive. For example, various polymeric materials such as cellulose acetate, polyethylene terephthalate, polycarbonate or polystyrene are suitable for the purpose of use. In this case, the above support may have a thickness which can freely be selected, but preferably in the range from about 50 microns to 250 microns. The one surface on the observation side of the support according to the present invention may also be freely worked depending on the purpose intended. Further, a light-transmissive undercoating layer may also be used, if desired, on the side of the support where a reagent layer is to be laminated to improve the adhesion between the reagent layer and the support.

The spreading layer of the present invention is selected from any of a number of layers, so long as it is provided with the performances as described in Japanese Patent Publication No. 21677/1978, namely:

(1) To distribute a constant volume of a fluid sample uniformly to a constant volume per unit area through the reagent layer;

(2) To remove substances or factors which interfere with the analytical reactions in the fluid sample;

(3) To effect a background action which reflects the measured light transmitted through the support during spectrophotometric analysis.

Accordingly, the spreading layer according to the present invention can perform all three functions mentioned above, but the three functions may also suitably be separated by the use of the layers having respective functions. Further, it is also possible to use a layer having two of the three functions and a layer having the other remaining function. For example, there may be mentioned a spreading layer of a non-fibrous porous medium called as the brush polymer comprising titanium dioxide and cellulose diacetate as disclosed in the above Patent, and the spreading layers of fibrous structure as disclosed in Japanese Provisional Patent Publications No. 24576/1981, No. 125847/1982 and No. 197466/1982. In particular, the above spreading layer of fibrous strucure is particularly useful as a material enabling also rapid delivery of blood cells.

The analytical element of the present invention can take any desired arrangement among various different arrangements. Further, it is also possible to constitute the analytical element in conformity with the object of the present invention by combining the reagent layer of the present invention optionally with various functional layers, reagent containing layers and members, as exemplified by the reagent layer, reflection layer, undercoating layer as disclosed in U.S. Pat. No. 3,992,158, radiation blocking layer as disclosed in U.S. Pat. No. 4,042,335, barrier layer as disclosed in U.S. Pat. No. 4,066,403, registration layer as disclosed in U.S. Pat. No. 4,144,306, migration inhibition layer as disclosed in U.S. Pat. No. 4,166,093 scintillation layer as disclosed in U.S. Pat. No. 4,127,499, scavenging layer as disclosed in Japanese Provisional Patent Publication No. 90859/1980 and destructive pod-like member as disclosed in U.S. Pat. No. 4,110,079, and the like.

The methods for preparation of the aforesaid layers and the methods for incorporation of the aforesaid layers in the analytical element of the present invention may be the same or similar to those as disclosed in said patents. In the aforesaid patents, there are also disclosed useful materials available in preparation of such layers.

After analytical results are obtained as detectable changes by use of the analytical element of this invention, measurements are performed according to reflective spectrophotometry, emission spectrophotometry, or reflective fluorescent spectrophotometry, etc. corresponding to various detectable changes. From the measured values thus obtained, the amounts of unknown analytes can be determined by referring to the calibration curve previously prepared.

The analytical element of the present invention having the constitution as described above can have its object accomplished by supplying a fluid sample from the side of the development layer and then observing the analytical reaction from the side of the transparent support.

A fluid sample to be applied to the analytical element according to the present invention may be used in an amount as desired, but preferably in an amount of about 50 μl to about 5 μl, more preferably about 20 μl to about 5 μl. Usually, it is preferred to use about 10 μl of a fluid sample.

The analytical reaction to be employed for the analytical element of the present invention may be determined suitably depending on the purpose of analysis. For example, it may be used for fields of clinical chemistry, particularly for analysis of biological fluid samples such as blood or components in urine.

The components in these fluid samples can be quantitatively analyzed on the acidic side by suitable choice of analytical reagents, and utilization of an immobile buffering agent is also possible.

The present invention is described in further detail by referring to the following Examples, by which the embodiments of the present invention are not limited at all.

EXAMPLE 1

On a transparent polyethyleneterephthalate support with a thickness of 180 microns, on which subbing had already been applied, there were successively coated the layers of the following compositions to prepare an analytical element.

(1) Reagent layer:

A reagent layer with a dried film thickness of about 20 microns, comprising:

Copoly(2-acrylamide-2-methylethane sulfonic acid—n-butyl acrylate) (Weight ratio 4:1): 21.5 $g/m^2$ 2,5-Dichlorophenyldizaonium chloride: 1.92 $g/m^2$ Octylphenoxy polyethoxyethanol (trade name: Triton ® X-100, produced by Rohm & Haas Co.): 0.8 $g/m^2$ (2) Spreading layer of fibrous structure:

A spreading layer of fibrous structure with a dried film thickness of about 160 microns, comprising:

Powdery filter (C) (produced by Toyo Roshi Co., 300 mesh or more): 91.0 $g/m^2$

Copoly(styrene—glycidyl methacrylate) (Weight ratio 95:5): 13.0 $g/m^2$

Octylphenoxy polyethoxyethanol: 0.5 $g/m^2$

With the use of the analytical element prepared with the above composition, various sera prepared to contain various concentrations of bilirubin were added dropwise each in an amount of 10 μl to the above spreading layer, and the reaction was carried out at 37° C. for 10 minutes, followed by measurement of the reflected density at 546 nm. The results are shown below.

| Concentration of bilirubin in serum (mg/dl) | Reflected density at 546 nm |
| --- | --- |
| 0 | 0.073 |
| 1.2 | 0.376 |
| 3.6 | 0.824 |
| 6.1 | 1.135 |
| 8.7 | 1.355 |
| 10.4 | 1.472 |

As apparently seen from the above results, good correlation is exhibited between the concentrations of bilirubin in serum and the reflected densities at 546 nm.

The above analytical element was also found to be good during storage without decomposition of the diazonium salt.

EXAMPLE 2

On a transparent polyethyleneterephthalate support with a thickness of 180 microns, on which subbing had already been applied, there were coated the reagent layer having the compositions shown in Table 1 and the spreading layer of the following compositions to prepare analytical elements Sample 2-1 and Sample 2-2.

TABLE 1

|  | Sample 2-1 | Sample 2-2 |
| --- | --- | --- |
| p-Nitrobenzene diazonium hexafluorophosphate ($g/m^2$) | 2.7 | 2.7 |

TABLE 1-continued

| | Sample 2-1 | Sample 2-2 |
|---|---|---|
| Copoly(2-acrylamide-2-methyl propane sulfonic acid - butyl acrylate) (Weight ratio 1:1) (g/m²) | 37.5 | 37.5 |
| Polyacrylamide (g/m²) | 12.5 | 12.5 |
| Triton X-100 (g/m²) | 7.5 | |
| Triton X-405 (g/m²) | | 10.0 |
| Spreading layer (provided by a method as disclosed in Japanese Patent Publication No. 21677/1978) | | |
| TiO₂ | 30.0 g/m² | |
| Cellulose diacetate | 3.7 g/m² | |

As the same procedures in Example 1, reflected density at 540 nm was measured from the side of the support to obtain Table 2.

TABLE 2

| Concentration of total bilirubin (mg/dl) | Reflected density | |
|---|---|---|
| | Sample 2-1 | Sample 2-2 |
| 0 | 0.41 | 0.43 |
| 0.4 | 0.50 | 0.52 |
| 1.6 | 0.62 | 0.58 |
| 3.8 | 0.74 | 0.64 |
| 8.7 | 0.95 | 0.76 |
| 12.7 | 1.07 | 0.82 |
| 19.1 | 1.26 | 0.84 |

EXAMPLE 3

On a transparent polyethyleneterephthalate support with a thickness of 180 microns, there were successively coated the layers of the following compositions to prepare an analytical element for urea analysis.

(1) Reagent layer (a dried film thickness of 75 μm):
Polyacrylamide: 11.90 g/m²
o-Phthalaldehyde: 13.65 g/m²
Sodium tri(isopropyl)-naphthalene sulfonate: 2.26 g/m²
Copoly(2-acrylamide-2-methylpropane sulfonic acid—acrylamide) (Weight ratio 1:1): 47.62 g/m²

(2) Spreading layer of fibrous structure:
Powdery filter (C) (produced by Toyo Roshi Co., 300 mesh or more): 91.0 g/m²
Copoly(styrene—glycidyl methacrylate) (Weight ratio 9:1): 13.9 g/m²
Triton X-100: 3.15 g/m²
N-(1-naphthyl)-N'-diethylethylene diamine hydrochloride: 8.04 g/m²

With the use of the analytical element prepared with the above composition, solutions prepared to contain various concentrations of urea were added dropwise each in an amount of 10 μl to the above spreading layer, and the incubation was carried out at 37° C. for 3 minutes, followed by measurement of the reflected densities at 650 nm and 540 nm. As a result, good correlation is exhibited between the reflected densities and the concentration level of urea, respectively.

We claim:

1. An analytical element comprising a support layer having an upper side and a lower side, a reagent layer which is positioned on one of said sides of said support and contains a reagent reactive with a component in a fluid sample, and a porous spreading layer which is positioned on the reagent layer on the opposite side to said support for permitting the component in said fluid sample to permeate into said reagent layer; wherein at least one of said layers contains at least 5% by weight of a copolymer formed by the polymerization of (i) at least 45% by weight of a copolymerizable ethylenically unsaturated acid with (ii) a copolymerizable ethylenically unsaturated monomer other than said copolymerizable ethylenically unsaturated acid.

2. An analytical element according to claim 1, wherein said copolymerizable ethylenically unsaturated acid is selected from the group consisting of the following formulas [I] and [II]:

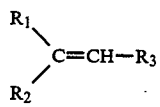

Formula [I]

wherein R₁ represents a carboxyl group, a sulfo group or a group having a carboxyl group or a sulfo group, R₂ represents a hydrogen atom or an alkyl group and R₃ represents a hydrogen atom or an alkoxycarbonyl group, and

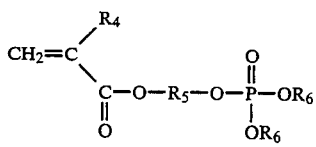

Formula [II]

wherein R₄ represents a hydrogen atom or a methyl group, R₅ represents an aliphatic hydrocarbon group having 2 to 10 carbon atoms or

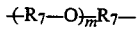

where R₇ is an aliphatic hydrocarbon group having 2 to 6 carbon atoms and m is an integer of 1 to 5 and R₆ represents a hydrogen atom.

3. An analytical element according to claim 1, wherein said copolymer is present in said reagent layer.

4. An analytical element according to claim 1, wherein said copolymerizable ethylenically unsaturated monomer (ii) is selected from the group consisting of an ethylenically unsaturated nitrile, a styrene, an ethylenically unsaturated acid ester, an ethylenically unsaturated acid amide, a conjugated diene, a vinyl heterocyclic compound, a halo-substituted ethylene and a crosslinkable monomer.

5. An analytical element according to claim 4, wherein said ethylenically unsaturated monomer (ii) is an ethylenically unsaturated nitrile represented by the following formula [III]:

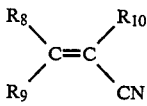

[III]

wherein R₈ and R₉ each represent a hydrogen atom or a halogen atom, R₁₀ represents a halogen atom, an alkyl group, an alkoxy group, an acyloxy group, an aryl group, a cyano group or a carbamoyl group.

6. An analytical element according to claim 4, wherein said ethylenically unsaturated monomer (ii) is a styrene represented by the following formula [IV]:

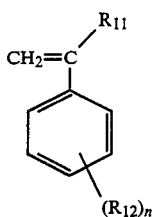

[IV]

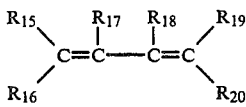

[VI]

wherein $R_{15}$ through $R_{20}$ individually represent a hydrogen atom, a halogen atom, an alkyl group, an aryl group, a cyano group or a group

—COOR$_{21}$ where $R_{21}$ represents an alkyl group.

wherein $R_{11}$ represents a hydrogen atom, a halogen atom or an alkyl group, $R_{12}$ represents a hydrogen atom, a halogen atom, an allkyl group, an alkoxy group, a cycloalkyl group, an alkoxycarbonyl group or an acryloxyalkyl group, and n is an integer of 1 to 5.

7. An analytical element according to claim 4, wherein said ethylenically unsaturated monomer (ii) is an ethylenically unsaturated acid ester represented by the following formula [V]:

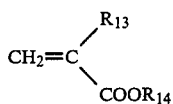

[V]

wherein $R_{13}$ represents a hydrogen atom or a methyl group, and $R_{14}$ represents an alkyl group or a phenyl group.

8. An analytical element according to claim 4, wherein said ethylenically unsaturated monomer (ii) is a conjugated diene represented by the following formula [VI]:

9. An analytical element according to claim 1, wherein said copolymer is copoly(2-acrylamide-2-methylethane sulfonic acid—n-butyl acrylate.

10. An analytical element according to claim 9, wherein the weight ratio of sulfonic acid to n-butyl acrylate in said copolymer is 4:1.

11. An analytical element according to claim 10, wherein said copolymer is present in said reagent layer.

12. An analytical element according to claim 1, wherein said copolymer is copoly(2-acrylamide-2-methylpropane sulfonic acid—butyl acrylate.

13. An analytical element according to claim 12, wherein the weight ratio of sulfonic acid to butyl acrylate in said copolymer is 1:1.

14. An analytical element according to claim 13, wherein said copolymer is present in said reagent layer.

15. An analytical element according to claim 1, wherein said copolymer is copoly(2-acrylamide-2-methylpropane sulfonic acid—acrylamide.

16. An analytical element according to claim 15, wherein the weight ratio of sulfonic acid to acrylamide is said copolymer is 1:1.

17. An analytical element according to claim 16, wherein said copolymer is present in said reagent layer.

* * * * *